United States Patent [19]

Edwards et al.

[11] Patent Number: 5,232,847
[45] Date of Patent: Aug. 3, 1993

[54] HUMAN TISSUE PLASMINOGEN ACTIVATOR ANALOGUE HAVING SUBSTITUTIONS AT AMINO ACID POSITIONS 66, 67 AND 68

[75] Inventors: Richard M. Edwards, Thame; Keith Dawson, Marlow; Anthony Fallon, Sandhills; Stewart Craig, Littlemore, all of England

[73] Assignee: British Bio-Technology Limited, Oxford, England

[21] Appl. No.: 613,908

[22] PCT Filed: Jun. 23, 1989

[86] PCT No.: PCT/GB89/00705

§ 371 Date: Dec. 11, 1990

§ 102(e) Date: Dec. 11, 1990

[87] PCT Pub. No.: WO89/12681

PCT Pub. Date: Dec. 28, 1989

[30] Foreign Application Priority Data

Jun. 24, 1988 [GB] United Kingdom ............... 8815135

[51] Int. Cl.⁵ .................. C12N 9/48; C12N 15/00
[52] U.S. Cl. ........................ 435/226; 435/212; 435/219; 424/94.63
[58] Field of Search ............ 424/94.63, 94.64; 435/226, 219, 212

[56] References Cited

U.S. PATENT DOCUMENTS

4,963,357 10/1990 Bell et al. ................ 424/94.64
5,108,901 4/1992 Anderson et al. ............. 435/23

FOREIGN PATENT DOCUMENTS

240334 10/1987 European Pat. Off. .
241209 10/1987 European Pat. Off. .
04722 8/1987 PCT Int'l Appl. .

Primary Examiner—Robert J. Hill, Jr.
Assistant Examiner—Marianne Porta Allen
Attorney, Agent, or Firm—Allegretti & Witcoff

[57] ABSTRACT

Tissue plasminogen activator (t-PA) analogues have at least one substitution in the growth factor (GF) domain that at least partially reduces hepatic receptor binding without substantially jeopardising physico-chemical stability in blood or fibrinolytic activity. This results in a longer plasma half life. Substitutions in the beta-sheet encompassing residues 63–72, especially at Leu 66 and/or Tyr 67 and/or Phe 68, are particularly preferred.

1 Claim, 10 Drawing Sheets

```
          63 64 65 66 67 68 69 70
           Q  Q  A  L  Y  F  S  D
          GCCAGCAGGCCCTGTACTTCTCAGATT
WT SEQUENCE ||||||||||  |   |||||||
          3'-gtcgtccgggagagctcgagtcta-5'
                          ↓

63 64 65 66 67 68 69 70
           Q  Q  A  L  S  S  S  D
          GCCAGCAGGCCCTcTcgagCTCAGATT
BBNT5     |||||||||||||||||||||||||
          3'-gtcgtccgggagagctcgagtcta-5'

63 64 65 66 67 68 69 70
           Q  Q  A  L  Y  F  S  D
          GCCAGCAGGCCCTGTACTTCTCAGATT
WT SEQUENCE ||||||||||  |   |||||||
          3'-gtcgtccgggagtggctgagtcta-5'
                          ↓

63 64 65 66 67 68 69 70
           Q  Q  A  L  T  D  S  D
          GCCAGCAGGCCCTcacCgaCTCAGATT
BBNT6     |||||||||||||||||||||||||
          3'-gtcgtccgggagtggctgagtcta-5'
```

FIG. 5a

```
           63 64 65 66 67 68 69 70
            Q  Q  A  L  S  S  S  D
           GCCAGCAGGCCCTCTCGAGCTCAGATT
BBNT5      |||||||||||||||||  ||||||||
        3'-cggtcgtccgggagagcgacagtctaa-5'

↓

63 64 65 66 67 68 69 70
            Q  Q  A  L  S  L  S  D
           GCCAGCAGGCCCTCTCGctgTCAGATT
BBNT11     |||||||||||||||||||||||||||
        3'-cggtcgtccgggagagcgacagtctaa-5'

63 64 65 66 67 68 69 70
            Q  Q  A  L  S  S  S  D
           GCCAGCAGGCCCTCTCGAGCTCAGATT
BBNT5      ||||||||||  |  |  ||||||||
        3'-cggtcgtccggctgctatggagtctaa-5'

↓

63 64 65 66 67 68 69 70
            Q  Q  A  D  D  T  S  D
           GCCAGCAGGCCgaCgatAcCTCAGATT
BBNT12     |||||||||||||||||||||||||||
        3'-cggtcgtccggctgctatggagtctaa-5'
```

FIG.5b

HUMAN TISSUE PLASMINOGEN ACTIVATOR ANALOGUE HAVING SUBSTITUTIONS AT AMINO ACID POSITIONS 66, 67 AND 68

This invention relates to proteinaceous molecules having improved t-PA-like activity and to nucleic acid (DNA and RNA) coding for all or part of them.

Tissue type plasminogen activator (t-PA) is a key component of the fibrinolytic system that is the natural counterpart to the clotting cascade in the blood. The maintenance of haemostasis is critically dependent on maintaining a correct balance between these two opposing tendencies In certain disorders such as acute myccardial infarction (MI), where the haemostatic balance has broken down locally resulting in the formation of a thrombus, the administration of fibrinolytic agents has been shown to be a beneficial therapy for the promotion of clot dissolution.

Such thrombolytic therapy has become relatively widespread with the availability of a number of such fibrinolytic agents such as streptokinase, urokinase, APSAC and t-PA itself. Human t-PA has theoretical advantages over other fibrinolytic agents in that it has fibrin affinity and preferentially activates plasminogen bound to the surface of a clot. This results in less systemic activation of plasminogen with correspondingly less depletion of fibrinogen and important clotting factors. In addition, t-PA is a natural human plasma protein and so is less likely to result in undesirable immune responses that may preclude against subsequent treatments with the same agent. The isolation and sequence analysis of both cDNA and genomic clones for t-PA has been described (Pennica et al 1983, Nature 301, 214; Ny et al. 1984, P.N.A.S. 81, 5355–5359) and so the amino acid sequence is known.

One of the major problems with t-PA for the treatment of MI or other thrombotic disorders comes from the extremely short plasma half-life of the molecule which in man is in the order of 5 min (Bounameaux et al in: Contemporary Issues in Haemostasis and Thrombosis Vol I p 85–91, 1985 (Collen et al eds, Churchill Livingstone). This results in the need to administer t-PA by infusion in large doses. The treatment is therefore expensive and requires that the patient be hospitalised before treatment can commence.

An improved thrombolytic agent with the beneficial properties of t-PA but with an extended plasma half-life is therefore sought.

Analysis of the t-PA molecule and its gene have revealed that it is a mosaic protein composed of 5 domains. The large serine protease domain can be recognised by its homology with other serine proteases and is the catalytically active domain involved in plasminogen activation. The 4 N terminal domains consist of a finger domain, so called because of its similarity to the type I homologies of fibronectin that are known to mediate the fibrin binding properties of that molecule, a growth factor domain, identified by its homology to a class of domain commonly observed in plasma proteins of which epidermal growth factor is the prototype sequence and two kringle domains which are homologous to domains in plasminogen, prothrombin and some other plasma proteins. A number of t-PA derivatives bearing deletions of one or more of the N-terminal domains have been described (Matsuo et al. 1985, FEBS Letters, 189, 145–149; van Zonneveld et al, 1986, P.N.A.S. 83, 4670–4674; Larsen et al, 1988, J. Biol. Chem. 263, 1023–1029; Browne et al, 1988, J. Biol. Chem. 263, 1599–1602; Kalyan et al 1988, J. Biol. Chem. 263, 3971–3978) and it is generally accepted through these and other studies that the finger domain and the second kringle domain are important mediators of fibrin binding and the fibrin stimulation of plasminogen activation by t-PA. The first kringle domain is of unknown function. It has been suggested that the growth factor domain may be involved in binding of t-PA to a receptor in the liver that mediates the clearance of t-PA from the circulation.

Various suggestions have been made therefore for deletion derivatives of t-PA that lack various N-terminal domains including the GF domain. In particular, evidence has been presented that such molecules may have an extended half life in vivo. Larsen et al describe variant t-PA derivatives that lack the finger domain, the GF domain or both. All three classes of variant were defective in fibrinolysis compared to t-PA when at low activator concentration although at higher concentration their properties were superficially similar to that of t-PA. Kalyan et al (supra) describe a similar deletion derivative lacking the finger and GF domain and demonstrate a 25 fold enhancement of half-life in a mouse model. The mutant molecule was defective in fibrin binding, however, as might be expected of a t-PA lacking the finger domain. Browne et al (supra) describe a t-PA derivative lacking the amino acid residues 51–87 that constitute the GF domain. The mutant t-PA was cleared much more slowly than wild-type t-PA in a guinea pig model. The problem with such mutants is that they are likely to be profoundly affected with respect to fibrin stimulation of catalytic activity, stability, overall conformation or a combination of all three. They are therefore of limited utility. Other suggestions have been made for t-PA derivatives with altered patterns of glycosylation obtained either by producing the t-PA from a different cell-line, by enzymic modification or by genetic modification of the glycosylation sites (Lau et al. 1987, Biotechnology, 5, 953–957). Such modified t-PA derivatives, in general do not have a dramatically extended plasma half life as the principal route of t-PA clearance is not mediated by a carbohydrate receptor.

It has, however, been reported that removal of the high mannose side chain from Asn 117 of t-PA either by treatment with the enzyme endo-$\beta$-N-acetylglucosaminidase H (Endo-H) (Tanswell et al, 1989, Fibrinolysis 3:79–84) or by mutation of Asn 117 to Gln (Hotchkiss et al, 1989, Thrombosis and Haemostasis 60:255–261) decreases the plasma clearance rate approximately two-fold.

Plasma levels of t-PA are normally at least partially regulated by natural t-PA inhibitors but therapeutic doses of t-PA are sufficiently high to overwhelm these inhibitors. It is possible though that analogues possessing a prolonged half-life may be administered in smaller doses than t-PA and may be affected by the inhibitors. It has been suggested that single chain analogues of t-PA may be less reactive with naturally occurring inhibitors of t-PA. Mutation of residues in the 274-277 region of tPA have been reported which prevent cleavage of the Arg 275 Ile 276 bond and result in active single chain t-PA (GB-A-2173804 and EP-A-0292009).

A t-PA derivative that possesses an extended half-life without deleterious changes in conformation, activity or physico-chemical stability is therefore sought.

The growth factor domain of t-PA is so called because of its primary sequence homology with that of Epidermal Growth Factor (EGF). Similar domains are found in a number of other plasma proteins such as the blood clotting proteins factors IX and X and the plasminogen activator urokinase. It was the observation that synthetic peptides corresponding to regions within the GF domain of urokinase competed with the binding of UK to its receptor on monocytes (Appella et al, 1987, *J. Biol. Chem.* 262, 4437-4440) that provided the first clue as to the domain's function. The peptide studies have not been repeated for t-PA but evidence in support of a receptor binding function for the GF domain comes from observations of the properties of t-PA derivatives lacking the GF domain which in general appear to have an extended plasma half-life, implying reduced rates of receptor mediated clearance. Such studies only provide circumstantial evidence, however, since detailed structural studies have not been performed to rule out the possibility of indirect effects on clearance rates. EP-A-0207589 discloses t-PA derivatives that are modified in the GF domain, specifically between residues 51-87 inclusive. The preferred embodiment of this disclosure involves the deletion of all or part of the domain although the possibility of amino acid substitutions was also included. In its broadest interpretation, this particular prior patent application encompasses 3620 possible single amino acid substitutions without providing a single example. A deletion of residues 51-87 was the only modification exemplified. The expression of this deletion variant in mouse C127 cells was disclosed and fibrinolytic activity detected using fibrin overlay zymography.

EP-A-0240334, a subsequent application, discloses t-PA derivatives modified specifically in the region between Tyr67 and Ser69. The preferred aspect of this disclosure is again a deletion of all or part of this region, although the specification also included unspecified modifications to the region. This broad disclosure in fact encompasses 8000 ($20^3$) possible t-PA derivatives without any further exemplification. EP-A-0240334 describes the expression of derivatives lacking residues 67-68 and 67-69 in mouse L929 cells and the observation of fibrinolytic activity associated with this expression using fibrin zymography. No significant biochemical characterisation was performed and no plasma half-life data was presented in either application.

Such deleted t-PA derivatives are limited in their utility, because the extent of the modification results in proteins that are radically different from the native molecule with far-reaching effects on stability, activity and immunogenicity.

Changes to the t-PA GF domain have now been developed which, whilst they are calculated to interfere with receptor binding, do not preclude the GF domain or the rest of the molecule from adopting a native conformation. The disclosures of EP-A-0207589 and EP-A-0240334 are not enabling for such changes since no account is taken of any structural constraints on the possible changes.

According to a first aspect of the present invention, there is provided a fibrinolytically active tissue plasminogen activator (t-PA) analogue having at least one substitution in the growth factor (GF) domain.

Such a substitution in the growth factor (GF) domain will generally at least partially reduce hepatic receptor binding without substantially jeopardising fibrinolytic activity. Similarly, physico-chemical stability in blood will for preference not be materially impaired. It is envisaged that there will usually be no net deletions, at least in the GF domain.

The design of modifications to the GF domain that are consistent with its ability to adopt a native conformation is a procedure that takes account of the predicted tertiary structure of the domain. A detailed study of the solution structure of EGF enables the building of a model of the t-PA GF domain upon which to base the rational design of such changes Of particular note is the region of beta sheet encompassing residues 63-72 which is a region implicated in receptor binding from the peptide studies on urokinase. Model building suggests that the two hydrophobic side chains of the residues Tyr 67 and Phe 68 present in the beta turn between the two strands of anti-parallel beta sheet are likely candidates to provide at least a part of the receptor binding region. A number of substitutions were therefore designed to alter the properties of this region without compromising its ability to adopt a beta turn.

Such subtle changes are important if the important features of full activity and stability are to be retained in the mutant derivative, as is preferred; and substitutions go against the teaching of the art discussed above in that all the modifications hitherto reported in this region have involved deletions. Even a small deletion comprising one or two amino acids in the beta turn itself, such as Tyr 67 or Phe 68 will undoubtedly cause the beta sheet that is the key structural feature of the GF motif to be one residue shorter and necessarily have some impact on the stability of the GF domain and hence the entire t-PA molecule.

The present invention encompasses modifications to the GF domain of t-PA that abrogate or greatly reduce receptor binding without jeopardising the stability, activity or overall conformation of the molecule by allowing the GF domain to adopt an otherwise native conformation. Fibrinolytic activity may be measured in a number of ways, for example in vitro by the clot lysis assay or the S-2251 chromogenic assay or in vivo by the rabbit model of peripheral arterial thrombosis. Fibrinolytic activity may be regarded as not substantially jeopardised if a t-PA analogue has at least 20%, 10%, 5% or even 1% of the fibrinolytic activity of wild type t-PA.

In a preferred embodiment the invention relates to single or multiple amino acid substitutions in the region between residues 63 and 72 inclusive that are consistent with its predicted secondary structure.

t-PA analogues in accordance with the invention may contain other modifications (as compared to wild type t-PA) which may be one or more additions, deletions and/or substitutions. For example, it is envisaged that t-PA inhibitors present in blood may have some noticeable effect on t-PA analogues of the present invention. With wild type t-PA their effect is not particularly significant because of the high therapeutic doses required to compensate for the very low half life of the active molecule. Preferred t-PA analogues in accordance with the invention therefore have a mutation in the serine protease domain that interferes with t-PA inhibitor binding. This could be around the 275-276 cleavage site or at another site in the protease domain.

Other plurally-modified t-PA analogues in accordance with the invention may include one or more modifications to prevent, reduce or alter glycosylation patterns. Such modification(s) may be at residues 117, 184 and/or 448. t-PA analogues incorporating modifications at one or more of these residues may have a longer half-life, reduced plasma clearance and/or higher specific activity.

According to a second aspect of the present invention, there is provided nucleic acid (which may be DNA or RNA) coding for a t-PA analogue as described above. Such nucleic acids may be in the form of vectors such as plasmids and in some embodiments is in expressible form. The invention extends to cell lines, particularly mammalian or other animal cell lines, expressing or capable of expressing such nucleic acid.

According to a third aspect of the invention, there is provided a t-PA analogue in accordance with the first aspect for use in human or veterinary medicine, particularly as thrombolytic agents.

According to a fourth aspect of the invention, there is provided a pharmaceutical composition comprising one or more t-PA analogues in accordance with the first aspect of the invention and a pharmaceutically or veterinarily acceptable carrier. Such a composition may be adapted for intravenous administration and may thus be sterile. Examples of compositions in accordance with the invention include preparations of sterile t-PA analogue(s) in isotonic physiological saline and/or buffer. The composition may include a local anaesthetic to alleviate the pain of injection.

t-PA analogues of the invention may be supplied in unit dosage form, for example as a dry powder or water-free concentrate in a hermetically sealed container such as an ampoule or sachet indicating the quantity of protein in activity units. Where a t-PA analogue is to be administered by infusion, it may be dispensed by means of an infusion bottle containing sterile water for injections or saline. Where it is to be administered by injection, it may be dispensed with an ampoule of water for injection or saline. The infusible or injectable composition may be made up by mixing the ingredients prior to administration.

The quantity of material to be administered will depend on the amount of fibrinolysis required, the required speed of action, the seriousness of the thromboembolic position and the size of the clot. The precise dose to be administered will, because of the very nature of the condition which t-PA analogues of the invention are intended to treat, be determined by the physician. As a guideline, however, a patient being treated for a mature thrombus will generally receive a daily dose of from 0.01 to 10 mg/kg of body weight either by injection in for example up to 5 doses or by infusion.

The invention may be used in a method for the treatment or prophylaxis of thrombotic disease, comprising the administration of an effective non-toxic amount of a t-PA analogue in accordance with the first aspect. According to a fifth aspect of the invention, there is therefore provided the use of a t-PA analogue as described above in the preparation of a thrombolytic agent.

According to a sixth aspect of the invention, there is provided a process for the preparation of a t-PA analogue in accordance with the first aspect, the process comprising coupling successive amino acid residues together. Although analogues may in principle be synthesised chemically, the route of choice will be ribosomal translation, preferably in vivo, of a corresponding nucleic acid sequence.

According to a seventh aspect of the invention, there is provided a process for the preparation of nucleic acid in accordance with the second aspect of the invention, the process comprising coupling successive nucleotides and/or ligating oligo- and/or polynucleotides together. Although nucleic acid molecules may be synthesised chemically, the route of choice will be to use a nucleic acid-directed polymerase, preferably in vivo.

Further preferred features of the invention will be apparent from the following description, which refers to the accompanying drawings, in which:

FIG. 5a shows primers used for t-PA mutagenesis in the construction of genes for t-PA analogues BBNT5 and BBNT6;

FIG. 5b shows primers used for t-PA mutagenesis in the construction of genes for t-PA analogues BBNT11 and BBNT12 (the relevant portion of the gene for BBNT5 is also shown as single stranded DNA from that gene was used as a template);

EXAMPLE 1

Construction of BBNT5

BBNT5 is a t-pA derivative in which amino acid residues 67 (tyr) and 68 (phe) have both been converted to serine residues. It was prepared by means of expression vector TND-HBB.

Figure 4:
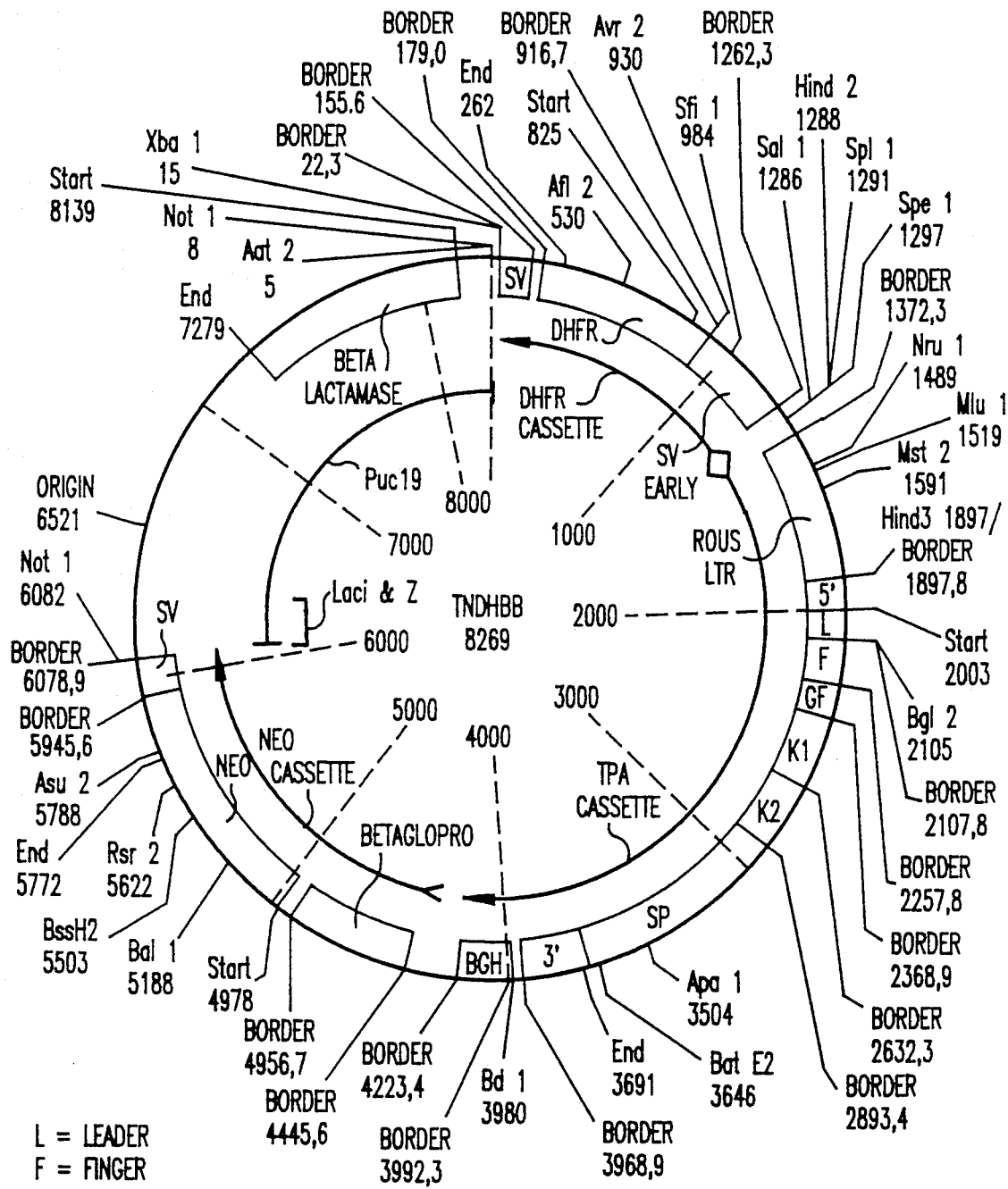
FIG. 4 shows a map of the expression vector TND-HBB.
Figure 6:
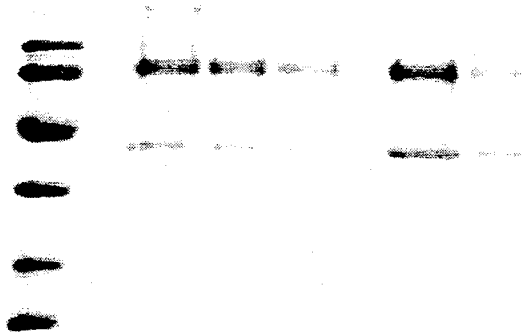
FIG. 6 shows an SDS PAGE gel showing purified t-PA analogue BBNT5.

TND-HBB is an expression vector suitable for the production of t-PA in mammalian cells. Briefly, the vector consists of an *E. coli* replicon containing a cDNA encoding t-PA that is transcribed from the LTR derived from RSV, with a polyadenylation signal from the bovine growth hormone gene included downstream. To allow for the selection of clones containing the expression cassette the selectable markers DHFR (dihydrofolate reductase, which confers the ability to grow in the presence of methotrexate) and NEO (neomycin phosphotransferase, which confers the ability to grow in the presence of the antibiotic G418) are also included. The DHFR gene is expressed from the SV40 early promoter and carries the SV40 early polyadenylation signal. The NEO gene is expressed from the mouse beta-globin promoter and carries the SV40 early polyadenylation signal. FIG. 4 is a schematic representation of TND-HBB. TND-HBB is a derivative of the plasmid TND that has been modified with respect to some of the restriction sites. The construction of the plasmid TND is disclosed by Connors et al (*DNA* 7 651–661 (1988)) and is the subject of U.S. patent application Ser. No. 137,892, filed Dec. 28, 1987; this publication and this U.S. patent application are incorporated by reference herein to the extent that the law allows. As will be apparent from a study of FIG. 4, the plasmid TND-HBB can be prepared from plasmid TND by commonly available methods well known to those skilled in the art.

Figure 1A:
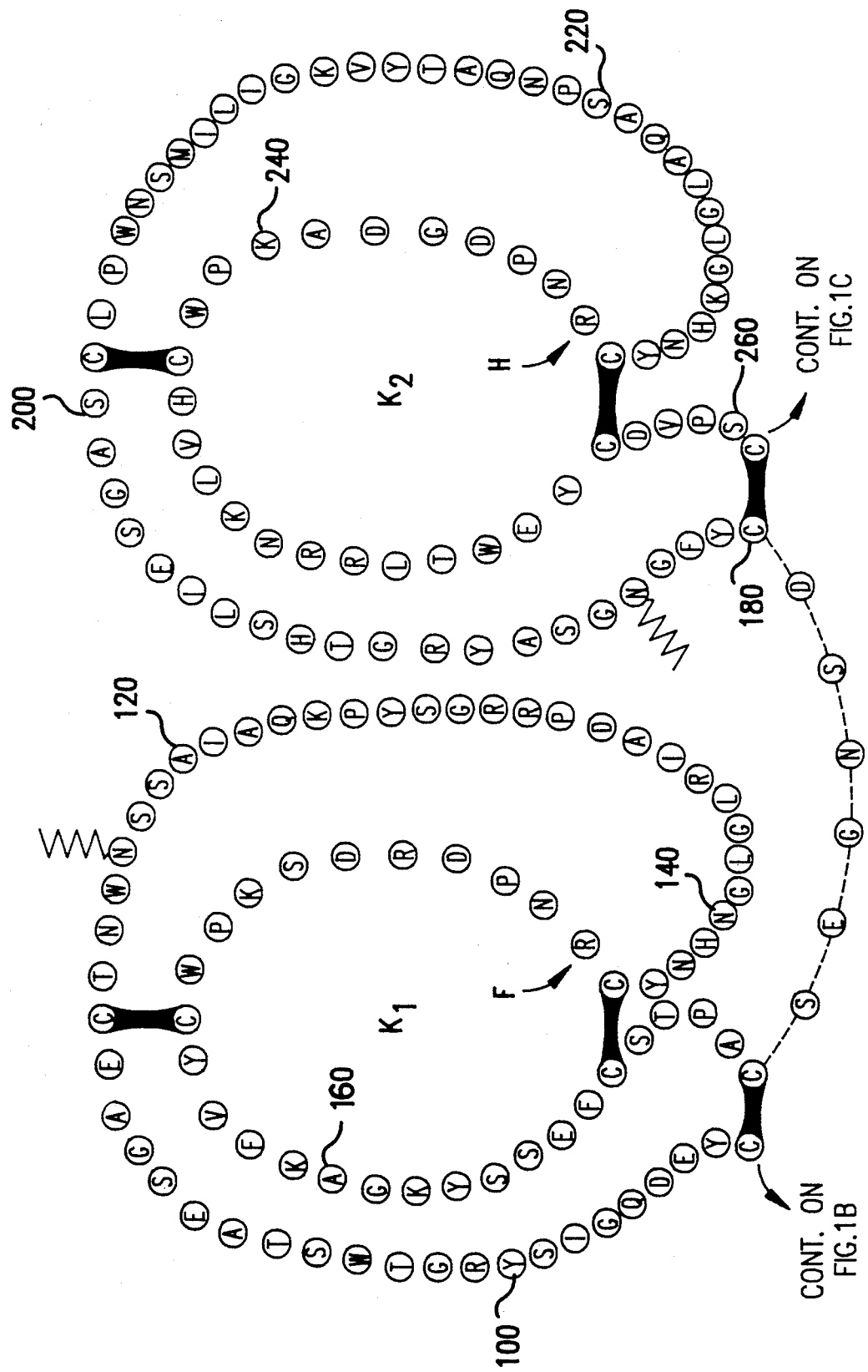
FIG. 1 shows diagrammatically the domain organisation and primary sequence of t-PA.
Figure 1B:
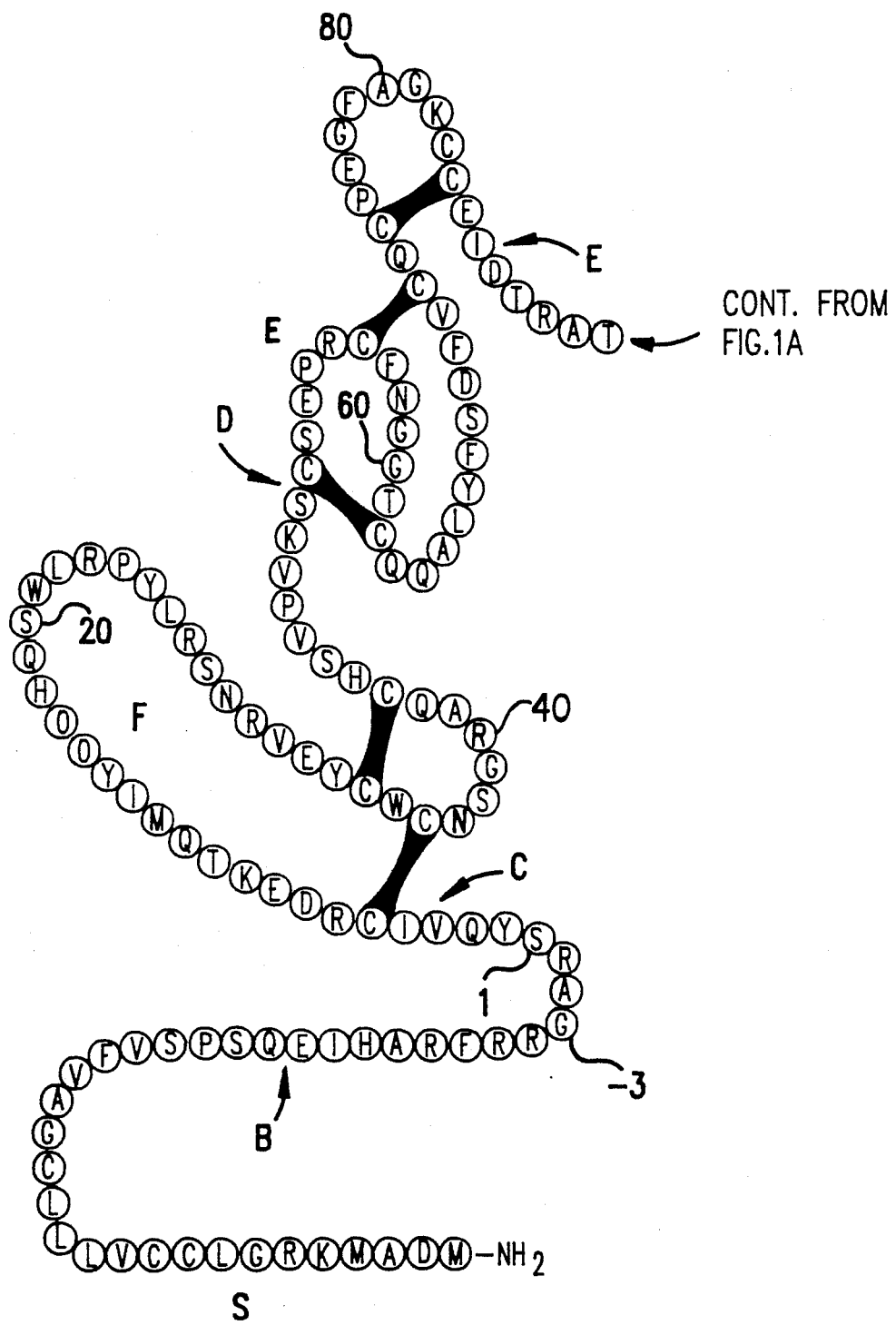
Figure 1C:
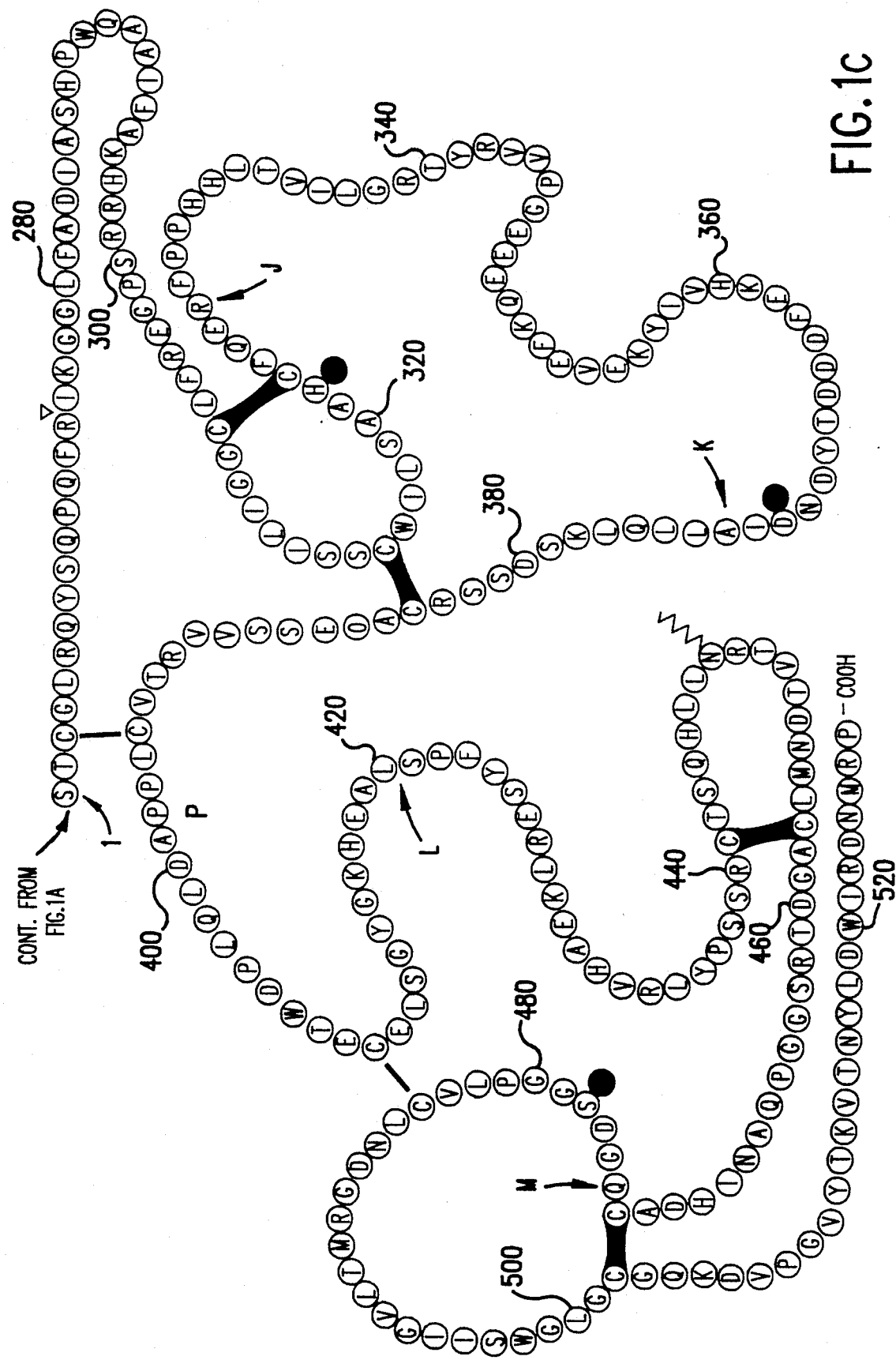
Figure 2:
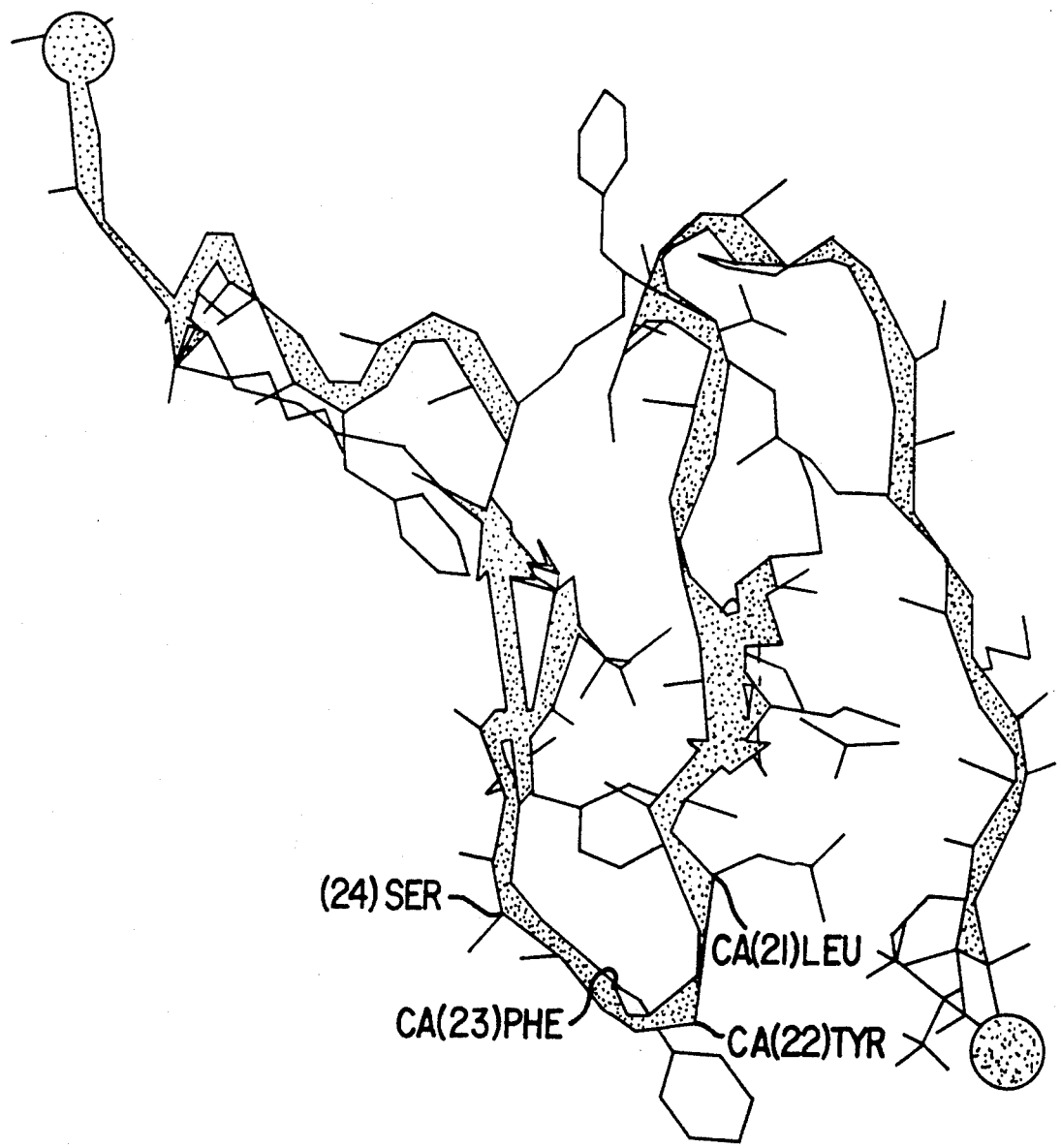
FIG. 2 shows a model of the t-PA GF domain.
Figure 3:
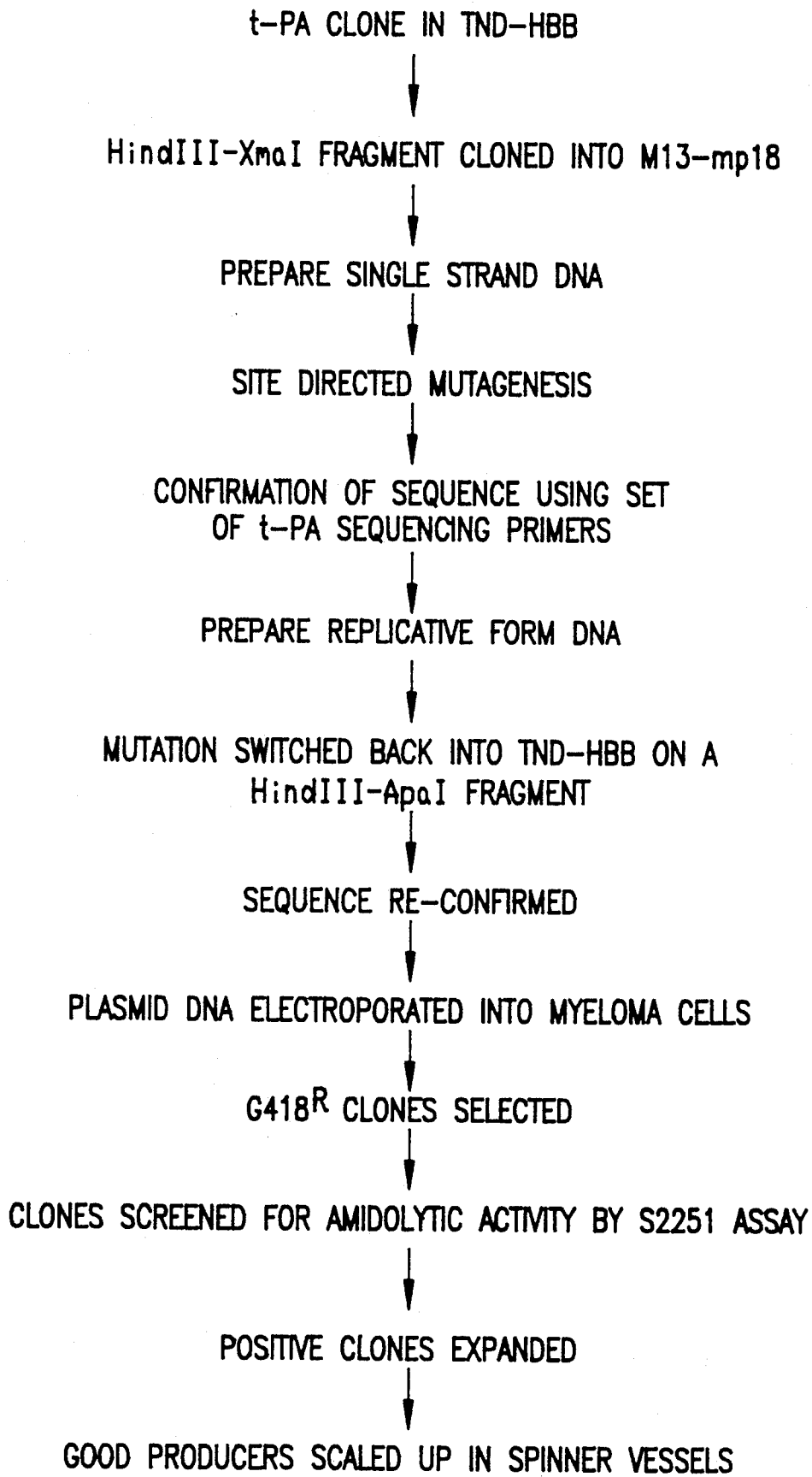
FIG. 3 shows in diagrammatic form an exemplary expression strategy.

This expression system is preferred because of its efficiency but its use is not intended to limit the scope of the present invention. There are now described many alternative methods of expressing genes in mammalian cells, and other hosts such as yeast and *E. coli* have also been employed to produce active t-PA. Such expression systems are well known to those skilled in the art of genetic engineering and have been at least partially documented by Gorman in *DNA cloning Vol II: A practical Approach* (D. M. Glover, ed. IRL Press, Oxford (1985) pp 143–190). t-PA cDNA usable in the present invention may have originated from HeLa cell mRNA; this has been described. Methods that can be used for the isolation of a cDNA corresponding to t-PA are also well documented. One example is given in GB-A-2119804, which again is herein incorporated by reference to the extent that the law allows. Another procedure that has been used is summarised in the following protocol:

1. Human liver was obtained at the time of emergency surgery from a 57 year old male trauma victim who died subsequently as a result of cardiac arrest.
2. The mRNA was prepared using the guanidine thiocyanate method (Chirgwin et al *Biochemistry* 10:5294 (1979)) and purified using an oligo-dT column (Aviv and Leder PNAS 69:1408 (1972)).
3. The cDNA library was prepared as described in the Amersham Protocol ("cDNA Synthesis and Cloning System", Amersham International plc, 1985) except that the double stranded cDNA was ligated to lambda-zap vector obtained from Stratagene (Short et al *Nucleic acids Res.* 16:7583 (1988)).
4. Plaques were screened for t-PA cDNA using the *Escherichia coli* BB4 strain by hybridisation to nitrocellulose replicates using $^{32}$P-labelled probes in 20% formamide, 5×SSC (SSC is 150 mM NaCl, 15 mM sodium citrate), 5×Denhardt's, 0.1% SDS and 0.2 mg/ml of *E. coli* tRNA at 42° C. Filters were washed using 2×SSC, 0.1% SDS at 42° C. to 45° C. Positive plaques were purified, subjected to automatic excision and the packaged recombinant plasmid clones or their subclones were sequenced by the dideoxy method of Sanger et al (Sanger et al *PNAS* 74:5463 (1977)) using dATP-5-Á-[35]thiophosphate The modification strategy in this example was to sub-clone the 1.7 Kb HindIII-XmaI fragment encompassing most of the t-PA cDNA from TND-HBB into the single stranded bacteriophage M13mp18 to facilitate the mutagenesis. Single stranded template DNA was prepared and the mutations made by oligonucleotide directed mismatch mutagenesis. In this case, a 24 base long oligonucleotide (5,ATCTGAGCT-CGAGAGGGCCTGCTG 3,) was used to direct the mutagenesis (amino acid residues 67 (Tyr) and 68 (Phe) both converted to Ser). These mutations also introduced sites for the restriction enzymes XhoI and SacI that could be used as genetic markers for the desired mutation. Clones carrying the desired mutation were identified by sequencing and then fully sequenced to ensure that no other mutation had been inadvertently introduced. RF DNA was then prepared and the mutation transferred into the expression vector by switching a HindIII—ApaI fragment. The sequence of the mutant t-PA cDNA was again confirmed in the expression vector prior to the commencement of expression studies. This modification protocol is outlined in FIG. 2.

TND-HBB plasmid DNA carrying the mutant t-PA gene was then linearised with the restriction endonuclease XbaI and introduced into the non-secreting, non-producing mouse myeloma cell line P3X63-Ag8.653 by electroporation. Plates yielding G418 resistant colonies were screened for t-PA activity by using the indirect amidolytic assay involving activation of plasminogen in the presence of fibrinogen and consequent cleavage of the chromogenic substrate S2251. Colonies producing t-PA were then re-cloned and the best producers scaled up in flasks and then spinner vessels to produce larger amounts of the t-PA derivative. t-PA was purified from the conditioned medium by affinity chromatography using Erythrina trypsin inhibitor immobilised on CNBr activated SEPHAROSE CL4B followed by elution using 3 M KSCN, desalting on SEPHADEX G25 and concentration by ultrafiltration. (The words SEPHAROSE and SEPHADEX are trade marks.) The purified t-PA derivative was then assayed for specific activity using the S2251 assay and assessed for receptor binding by its ability to compete with $I^{125}$ labelled t-PA for binding to rat liver hepatocytes. The in vivo efficacy at clot lysis was determined in a rabbit femoral artery model that also permitted the measurement of the plasma half-life as determined by following both amidolytic activity and t-PA antigen using an ELISA assay.

All the above methodologies have been described elsewhere and are well known to those involved in the field. Detailed protocols are outlined below where minor modifications have been made to published procedures.

METHODS

The techniques of genetic manipulation, expression and protein purification used in the manufacture of this modified t-PA derivative, as well as those of the other examples to follow, are well known to those skilled in the art of genetic engineering. A description of most of the techniques can be found in one of the following laboratory manuals: Molecular Cloning by T. Maniatis, E. F. Fritsch and J. Sambrook published by Cold Spring Harbor Laboratory, Box 100, New York, or Basic Methods in Molecular Biology by L. G. Davis, M. D. Dibner and J. F. Battey published by Elsevier Science publishing Co. Inc. New York.

Additional and modified methodologies are detailed below.

1) Oligonucleotide Synthesis

The oligonucleotides were synthesised by automated phosphoramidite chemistry using cyanoethyl phosphoramidtes. The methodology is now widely used and has been described (Beaucage, S. L. and Caruthers, M. H. Tetrahedron Letters. 24, 245 (1981)).

2) Purification of Oligonucleotides

The oligonucleotides were de-protected and removed from the CPG support by incubation in concentrated NH$_3$. Typically, 50 mg of CPG carrying 1 micromole of oligonucleotide was de-protected by incubation for 5 hr at 70° in 600 μl of concentrated NH$_3$. The supernatant was transferred to a fresh tube and the oligomer precipitated with 3 volumes of ethanol. Following centrifugation the pellet was dried and resuspended in 1 ml of water. The concentration of crude oligomer was then determined by measuring the absorbance at 260 nm.

For gel purification 10 absorbance units of the crude oligonucleotide were dried down and resuspended in 15 mcl of marker dye (90% de-ionised formamide, 10 mM tris, 10 mM borate, 1 mM EDTA, 0.1% bromophenol blue). The samples were heated at 90° for 1 minute and then loaded onto a 1.2 mm thick denaturing polyacrylamide gel with 1.6 mm wide slots. The gel was prepared from a stock of 15% acrylamide, 0.6% bisacrylamide and 7M urea in 1 X TBE and was polymerised with 0.1 % ammonium persulphate and 0.025% TEMED. The gel was pre-run for 1 hr. The samples were run at 1500 V for 4-5 hr. The bands were visualised by UV shadowing and those corresponding to the full length product cut out and transferred to micro-testubes. The oligomers were eluted from the gel slice by soaking in AGEB (0.5 M ammonium acetate, 0.01 M magnesium acetate and 0.1 % SDS) overnight. The AGEB buffer was then transferred to fresh tubes and the oligomer precipitated with three volumes of ethanol at −70° for 15 min. The precipitate was collected by centrifugation in an Eppendorf microfuge for 10 min, the pellet washed in 80 % ethanol, the purified oligomer dried, redissolved in 1 ml of water and finally filtered through a 0.45 micron micro-filter. The concentration of purified product was measured by determining its absorbance at 260 nm.

3) Kinasing of Oligomers 250 pmole of oligomer was dried down and resuspended in 20 μl kinase buffer (70 mM Tris pH 7.6, 10 mM MgCl$_2$, 1 mM ATP, 0.2 mM spermidine, 0.5 mM dithiothreitol). 10 u of T4 polynucleotide kinase was added and the mixture incubated at 37° for 30 min. The kinase was then inactivated by heating at 85° for 15 min.

4) Dideoxy sequencing

The protocol used was essentially as has been described (Biggin, M. D., Gibson, T. J., Hong, G. F. *P.N.A.S.* 80 3963-3965 (1983)). Where appropriate the method was modified to allow sequencing on plasmid DNA as has been described (Guo, L-H., Wu, R. *Nucleic Acids Research* 11 5521-5540 (1983).

5) Transformation

Transformation was accomplished using standard procedures. The strain used as a recipient in the cloning using plasmid vectors was HW87 which has the following genotype:

araDI 39(ara-leu)de17697 (lacIPOZY)de174 galU
galK hsdR rpsL srl recA56

HW1085 is a mutL derivative of *E.coli* that carries an F' to allow infection by male specific phage. Its principal benefit is that the mutL mutation leads to a higher frequency of mutants in site directed mutagenesis. JM103 is a standard recipient strain for manipulations involving M13 based vectors.

6) Site Directed Mutagenesis

Kinased mutagenesis primer (10pmole) was annealed to the single stranded template DNA (5 μg) along with universal sequencing primer (10 pmole) in a final reaction mix of 10 μl containing 70 mM Tris, 10 mM MgCl$_2$. The reaction mixture in a polypropylene micro-testube (Eppendorf) was placed in a beaker containing 250 ml of water at 90°. The beaker was covered with polystyrene and allowed to slow cool to 30° with stirring. The annealed mixture was then placed on ice and the following reagents added: 1 mcl of 10×TM (700 mM Tris, 100 mM MgCl$_2$ pH7.6), 1 mcl of a mixture of all 4 deoxyribonucleotide triphosphates each at 5mM, 2 μl of 50 mM dithiothreitol, 1 μl of T4 DNA ligase (100u), 0.5 μl Klenow fragment of DNA polymerase and 4.5 μl of water. The polymerase reaction mixture was then incubated at 12° for 4 hr. After the reaction was complete, 180 mcl of TE (10 mM Tris, 1 mM EDTA pH8.0) was added and the mutagenesis mixture stored at −20°.

For the isolation of mutant clones the mixture was then transformed into the mutL recipient HW1085 as follows. A 5 ml overnight culture of HW1085 in 2×YT (1.6% Bactotryptone, 1% Yeast Extract, 1% NaCl) was diluted 1 in a 1000 into 50 ml of pre-warmed 2×YT. The culture was grown at 37° with aeration until the A600 reached 0.4. The cells were pelleted and resuspended in 0.5 vol of 50 mM CaCl$_2$ and kept on ice for 15 min. The cells were then re-pelleted at 4° and resuspended in 2.5 ml cold 50 mM CaCl$_2$. For the transfection, 0.25, 1, 2, 5, 20 and 50 μl aliquots of the mutagenesis mixture were added to 200 μl of competent cells which were then kept on ice for 30 min. The cells were then heat shocked at 42° for 2 min. To each tube was then added 3.5 ml of YT soft agar containing 0.2 ml of a late exponential culture of JM103, the contents were mixed briefly and then poured onto the surface of a pre-warmed plate containing 2×YT solidified with 1.5% agar. The soft agar layer was allowed to set and the plates then incubated at 37° overnight.

Single strandad DNA was then prepared from isolated clone as follows: Single plaques were picked into 4 ml of 2×YT that had been seeded with 10 μl of a fresh overnight culture of JM103 in 2×YT. The culture was shaken vigorously for 6 hr. 0.5 ml of the culture was then removed and added to 0.5 ml of 50% glycerol to give a reference stock that was stored at −20°. The remaining culture was centrifuged to remove the cells and 1 ml of supernatant carrying the phage particles was transferred to a fresh Eppendorf tube. 250 μl of 20% PEG6000, 250mM NaCl was then added, mixed and the tubes incubated on ice for 15 min. The phage were then pelleted at 10,000rpm for 10 min, the supernatant discarded and the tubes re-centrifuged to collect the final traces of PEG solution which could then be removed and discarded. The phage pellet was thoroughly resuspended in 200 μl of TEN (10 mM Tris, 1 mM EDTA, 0.3 M NaOAc). The DNA was isolated by extraction with an equal volume of Tris saturated phenol. The phases were separated by a brief centrifugation and the aqueous phase transferred to a clean tube. The DNA was re-extracted with a mixture of 100 μl of phenol, 100 μl chloroform and the phases again separated by centrifugation. Traces of phenol were removed by three subsequent extractions with chloroform and the DNA finally isolated by precipitation with 2.5 volumes of ethanol at −20° overnight. The DNA was pelleted at 10,000 rpm for 10 min, washed in 70% ethanol, dried and finally resuspended in 50 μl of TE.

7) Electroporation

The mouse myeloma cell line p3x63-Ag8.653 was grown and harvested in mid log growth phase by centrifugation. The cells were resuspended in PBS and a viable cell count was made. The cell were then pelleted and resuspended at 1×10 7 cells/ml. 40 μg of linearised DNA was added to 1 ml of cells and allowed to stand on ice for 15 min. One pulse of 800 V/ 25 μF was administered to the cells using a commercially available electroporation apparatus (BIORAD GENE PULSER—trade mark). The cell were incubated on ice for a further 15 min and then plated into 10×96 well plates with 200 μl of conditioned medium per well (DMEM, 5% FCS, Pen/Strep, glutamine) and incubated overnight. After 24 hr, 100 μl medium was removed from each well and replaced with 100 μl of selective media containing G418 at 400 μg/ml. The feeding regime was followed for a further 4 successive days.

After about 14 days G418 resistant colonies are evident in some of the wells. The plates were screened for t-PA activity by removing an aliquot of medium from each well and assaying using the S2251 assay. Clones producing t-PA were scaled up and the expression level monitored to allow the selection of the best producer.

8) Purification of t-PA Variants

Erythrina trypsin inhibitor (ETI) obtained commercially from American Diagnostica is coupled to CNBr activated SEPHAROSE-4B (Pharmacia) according to the manufacturers instructions. A loading of 5 mg protein per ml of gel is used. The column is then equilibrated with at least 10 column volumes of PBS at pH7.5. The column is loaded with conditioned medium using 1 ml of gel for each 400 mcg of t-PA as determined using the S2251 assay and a Kabi-Vitrum standard of 700,000 u/mg. Typically, 3 l of conditioned medium containing 1 mg/ml t-PA is applied to a 10 ml column (H:D=4) at a linear flow rate of 85 ml/cm/hr at 4°. After loading is complete, the column is washed with a minimum of 5 column volumes of PBS pH7.5 until non-specifically bound protein ceases to be eluted from the column. Elution of the bound t-PA is achieved through the use of 3M KSCN in 0.15M NH4OAc buffer pH 5.3 containing 1 mM EDTA. The solution is filtered using a PTFE membrane, pore size 0.45 micron prior to use. Elution requires two column volumes and is carried out at a linear flow rate of 34 ml/cm/hr. The purified fractions of t-PA derivative are stored frozen at −20°.

Following elution, the column is regenerated by washing with 5 volumes of 0.1 M NH4O Ac pH 4.0 followed by 5 volumes of 0.1 M Tris HCl pH 8.0.

When 10 mg of t-PA derivative had been accumulated at sufficient purity as judged by homogeneity on SDS PAGE and with a specific activity of 300–700,000 u/mg, the KSCN was removed and replaced by 0.1 M NH4OAc buffer pH4.0 by chromatography on Sephadex G-25M. Typically, 25 ml of t-PA derivative at a concentration of 0.4 mg/ml was applied to a 100 ml bed volume column (2.5×20 cm) equilibrated in 0.1 M NH4OAc pH4.0. Chromatography is carried out at room temperature at a linear flow rate of 40 ml/cm/hr. Fractions containing t-PA derivative are pooled and concentrated at 4° to 0.75–1.0 mg/ml protein as determined using Bradford reagent (Biorad) using an Amicon stir cell with a YM10 membrane at 20 psi.

EXAMPLE 2

Construction of BBNT6

The procedure of Example 1 was generally followed except that the primer used was the 24mer (5' ATCTGAGTCGGTGAGGGCCTGCTG 3'). The mutagenesis and expression studies were performed as for BBNT5 (Example 1). In the resulting mutant derivative of t-PA, Tyr67 was converted to threonine and Phe68 to aspartic acid.

EXAMPLE 3

Construction of BBNT11

The procedure of Example 1 was generally followed, except that a 27 base oligonucleotide was used to prime on a single stranded DNA template obtained from Example 1, which generated BBNT5. The 27mer used was (5'AATCTGACAGCGAGAGGGCCTGCTGGC 3'). In this derivative, Tyr67 was converted to serine and Phe68 to leucine. The mutation was designed to remove the XhoI and SacI sites introduced in the construction of BBNT5 (Example 1).

EXAMPLE 4

Construction of BBNT12

This derivative in which Leu66 is converted to aspartic acid, Tyr67 is converted to aspartic acid and Phe68 to threonine was constructed in analogous fashion to BBNT11, the subject of Example 3, using as a primer the 27 base oligonucleotide (5'AATCTGAGGTATCGTCGGCCTGCTGGC 3').

EXAMPLE 5

Construction of a Mutant BBNT12 Derivative Lacking the Glycosylation Site at N117

Wild-type t-PA is normally glycosylated at 3 sites, namely N117, N184 and N448. The site at N117 is subject to a high mannose form of glycosylation and it has been proposed that this, via liver mannose receptors, contributes to the high rate of t-PA plasma clearance. A double mutant combining a mutation in the GF domain that extends plasma half-life with a mutation that affects the glycosylation pattern of the molecule and thus interferes with a different clearance mechanism would result in a molecule with an even greater plasma half-life. This type of t-PA combination mutant was exemplified by removing the high mannose glycosylation site in BBNT12 (Example 4).

A second site mutation that converts N117 to Q in the mutant t-PA derivative BBNT12 was introduced, thereby abolishing the glycosylation site at this position. This derivative, GF13, was constructed using a 21 base oligonucleotide primer with the sequence 5' CGCGCTGCTCTGCCAGTTGGT 3'.The mutagenesis and expression studies were performed as for BBNT5 (prepared in Example 1).

EXAMPLE 6

Construction of a t-PA Deletion Mutant Lacking Residues Y67 and F68—This is a Comparison Example For comparative purposes, one of the mutant t-PA derivatives described by Browne et al in EP-A-0240334 has been constructed. This patent application describes t-PA analogues carrying deletions in the G domain. Specifically, residues Y67 and F68 were deleted using site-directed mutagenesis, for which a 23 base oligonucleotide primer with the sequence 5' CACGAAATCTGACAGGGCCTGCT 3' was employed. The mutagenesis and expression studies were carried out as described for BBNT5. The resultant mutant t-PA analogue was named GF6.

EXAMPLE 7

Expression of the Modified t-PA Genes

The region encompassing the desired mutations was introduced into the t-PA expression vector and the sequence of each of the mutant t-PA gene was confirmed. Linearised plasmid was then introduced into myeloma cells by electroporation and G418 resistant clones producing the mutant t-PA identified by testing for protease activity using the S2251 assay.

Those clones producing high levels of the t-PA derivative were scaled up progressively until 5 liters of medium could be harvested. The modified t-PA was then purified and its specific activity determined (see Table 1).

TABLE 1

| Variant | Change | | | | Specific Activity U/mg S2251 assay |
|---|---|---|---|---|---|
| | 66 | 67 | 68 | 69 | |
| WT t-PA | Leu | Tyr | Phe | Ser | 532000 |
| BBNT5 | Leu | Ser | Ser | Ser | 440000 |
| BBNT6 | Leu | Thr | Asp | Ser | 473000 |
| BBNT11 | Leu | Ser | Leu | Ser | 427000 |
| BBNT12 | Asp | Asp | Thr | Ser | 304000 |
| GF6 | Leu | — | — | Ser | 490000 |
| GF13 | Asp | Asp | Thr | Ser* | 440000 |

*Asn 117 changed to Gln

EXAMPLE 8

Chromogenic Assay for Variant t-PA Derivatives

Plasminogen activation by t-PA variants was measured using S2251 (Kabi), the specific tripeptide chromogenic substrate for plasmin. Aliquots of the sample (50 mcl) were mixed with 50 μl of buffer (50 mM Tris, 0.1 M EDTA, 0.0005% Triton X100, pH 8.0) containing 0.6 mM S2251, 0.5 μM plasminogen and 0.4 mg/ml fibrinogen in 96 well plates (Costar). The plates were incubated at 37° for 30 min. The reaction was terminated by adding 50 μl of 0.5 M acetic acid and the absorbance read at 405 nm using an automatic plate reader (Dynatech). Quantitation was performed by comparison with a standard t-PA preparation. The specific activity of 9 BBNT5 measured in the chromogenic assay was $4.4 \times 10^5$ IU/mg relative to the WHO t-PA standard (83/517). This value is approximately 82% for that of CHO wild type 12 t-PA ($5.32 \times 10^5$ IU/mg).

EXAMPLE 9

Determination of Hepatocyte Binding Properties of BBNT5 and Other Analogues

The ability of BBNT5 to compete with the uptake of tissue plasminogen activator by freshly isolated rat hepatocytes was examined. Hepatocytes are isolated from the livers of Sprague Dawley rats by perfusing the liver with collagenase (Rush and Alberts *Life Sci.* 40:679-685, 1987). The cells are then incubated at 37° with 0.01 nM $^{125}$I-t-PA (Bugelski et al Uptake of human recombinant tissue-type plasminogen activator by rat hepatocytes in vivo: an electron microscope autoradiographic study. *Thrombosis Research* 53 287-303 (1989)) at $1 \times 10^6$ cells/ml in Kreb's-Henseleit buffer container 2% bovine serum albumin. After washing, cell associated counts are measured by gamma scintigraphy. Hepatocytes typically take up on the order of 2 fmoles t-PA/$10^6$ cells over a 45 minute incubation. Addition of 200 nmolar cold wild type t-PA decreases uptake by up to 75%. In contrast, addition of 200 nmolar BBNT5 does not compete with uptake of $^{125}$I-t-PA. This suggests that BBNT5 is not taken up by hepatocytes via the high affinity uptake process for wild type t-PA recently described (Bakhit et al, *J. Biol. Chem.* 262:8716-8720, 1987). BBNT6, 11 and 12 and GF6 also did not compete with uptake of 125I-t-PA, by hepatocytes.

EXAMPLE 10

Determination of Clot Lysis Ability of BBNT5 and Other Analogues

The ability of BBNT5 to lyse clots was compared with that of wild-type t-PA in a rabbit femoral artery model.

Male New Zealand white rabbits weighing 0.6 to 1.5kg were anaesthetised with 35 mg/kg of sodium pentobarbital via the marginal ear vein. Body temperature was maintained at 39.5° C. with a Yellow Spring THERMISTEMP (trade mark) temperature controller (Model 71A) coupled with an incandescent lamp. The carotid artery was cannulated for recording of arterial blood pressure with a Stratham P50 transducer. Concomitant with pressure recording, a solution of pentobarbital sodium was infused through this cannula at a rate of 6 mg/kg/hr in a volume of 0.6 ml/hr. This infusion was necessary to maintain the anaesthetic level of the rabbit and to maintain patency of the cannula.

Figure 7:
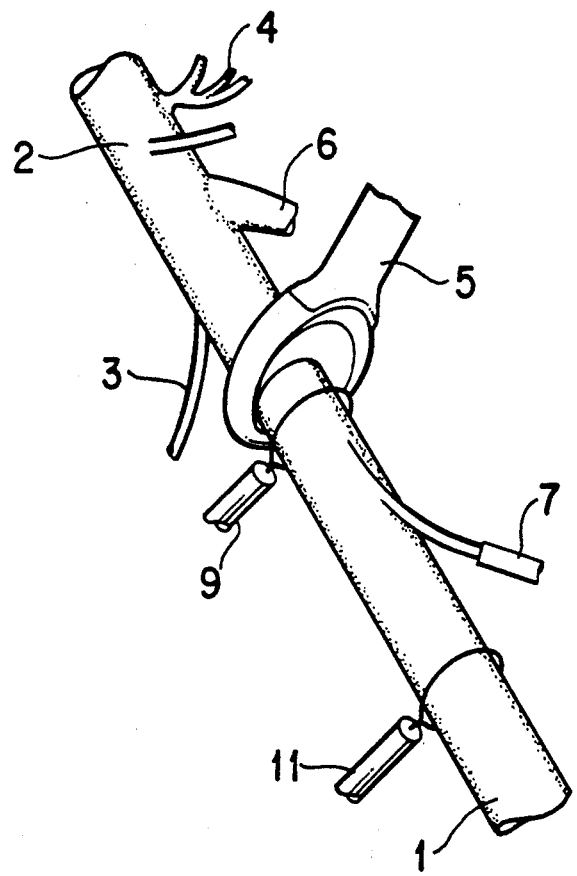
FIG. 7 shows a schematic perspective view of the right femoral artery system of the rabbit, in which the in vivo thrombolytic efficacy of analogues of the invention may be assessed.

The right femoral artery 1 (FIG. 7) was isolated distally from the inguinal ligament 2 and traumatised distally from the lateral circumflex artery 3 by rubbing the artery on the jaw of a forceps. FIG. 7 also shows the position of the inferior epigastric artery 4 and the deep femoral artery 6. An electromagnetic flow probe 5 (Carolina Medical Electronics, Inc., King, N.C., USA) was placed distal to the lateral circumflex artery 3 to monitor femoral artery blood flow. The superficial epigastric artery 7 was cannulated for induction of a thrombus. Thrombi were localised distally from the lateral circumflex artery 3 with proximal and distal snares 9 and 11 approximately one cm apart and induced by the sequential injection of 5 units of human thrombin (5 μl), 5 μl of 0.25 M $CaCl_2$, and 10 to 20 μl of arterial blood sufficient to distend the artery 1. After 30 minutes the snares 9 and 11 were released and the flow monitored for an additional 30 minutes to confirm total obstruction of flow by the thrombus.

t-PA (wild type - CHO) or analogues were infused i.v. for 90 min at doses of 5.0 or 10.0 μg/kg/min. Thrombolysis was assessed as restoration of femoral artery blood flow in response to t-PA or analogue infusion. Reperfusion (restoration of flow) was judged complete when femoral artery blood flow returned to at least 50% of control flow and was maintained at that level. The infusion was terminated at 90 min. and the femoral arterial blood flow was monitored for another 30 min. At the end of the 30 min observation period after t-PA or analogue infusion, the animal was sacrificed and the residual thrombus was excised, blotted and weighed immediately. The results are shown in Table 2 below.

TABLE 2

Comparison of t-PA Analogues and Wild Type t-PA in the Rabbit Model of Femoral Arterial Thrombosis

| Compound (μg/kg/min) | Reperfusion Incidence | Time to Reperfusion (min) | Thrombus Weight (mg) |
|---|---|---|---|
| BBNT5(10) | 7/8 (88%) | 48.9 ± 6.4 | 1.1 ± 0.5 |
| w/t t-PA(10) | 19/21 (90%) | 58.7 ± 4.9 | 2.0 ± 0.5 |
| Saline | 0/5 (0%) | — | 9.2 ± 0.9 |
| BBNT6(5) | 3/8 (37.5%) | 82 ± 6 | 4.9 ± 1.02 |
| BBNT11(5) | 1/4 (25%) | 69 | 5.4 ± 1.9 |
| BBNT12(5) | 7/8 (87.5%) | 71.9 ± 10 | 1.6 ± 0.7 |
| w/t t-PA(5) | 8/24 (33%) | 64.4 ± 6.6 | 4.9 ± 0.7 |
| GF6(5) | 1/4 (25%) | 90 | 2.7 ± 0.6 |

It can be seen that several substitution analogues are more effective than t-PA at inducing reperfusion and that a deletion mutant GF6 (deletion of Tyr 67 and Phe 68) as described in EP-A-0240334 is not better than t-PA.

EXAMPLE 11

Pharmacokinetic Analysis of BBNT5 in the Rabbit

Collection of Blood Samples and Determination of Active t-PA

Concentration in Plasma: Blood samples were collected through an indwelling catheter in the carotid artery at 0, 5, 8, 11 and 14 min during infusion of t-PA and at 1, 2, 3, 5, 10, 15, 20, 30, and 60 min after the termination of infusion. A two-syringe technique was used to avoid contamination of samples. 0.5 ml blood was mixed with 70 μl of chilled 100 mM trisodium citrate and centrifuged immediately in an Eppendorf microfuge for 1 min. The plasma was removed immediately, preserved with an equal volume of IM acetic acid/sodium acetate (pH 3.8), quick-frozen and stored at $-80°$ C. until assay. The concentration of functionally active t-PA in plasma was determined by a modified and validated S-2251 chromogenic assay (Crysler & Fong, *Pharmacologist* 28 117 (1986)). A standard curve in pooled citrated rabbit plasma was constructed with the same batch of t-PA that was used for in vivo administration. A typical assay mixture of 0.1 ml volume contained the following: 0.5 μM (0.045 mg/ml) human glu-plasminogen, 0.9 μM (0.3 mg/ml fibrinogen), 3mM S-2251, 0.005% Triton X-100, 0.05 mM EDTA, 0.05 mg/ml anti-t-PA or normal immunoglobulin. Anti-t-PA was included in duplicate samples to subtract non-t-PA derived amidolytic activity. A standard curve of 0.30 IU/ml concentration required an incubation time of 90 min at 37° C. Assay was stopped by the addition of 0.1 ml of 0.5 M acetic acid. Colour development was quantitated at 410 nm on a Dynatech MR 600 plate reader with reference wavelength at 490 nm.

Pharmacokinetic Data Analysis: Pharmacokinetic parameters were estimated with the PHARM data analysis software (Gomeni R: PHARM, An Interactive Graphic Program for Individual and Population Pharmacokinetic parameter Estimation. *Comput Biol Med* 14: 25, 1980). The half-life was estimated by unweighted linear regression of the log-transformed post-infusion data. The plasma clearance ($Cl_s$) and the steady-state volume of distribution ($VD_{ss}$) were calculated by non-compartmental methods (Gibaldi M, Perrier D: Phamacokinetics 2nd Edition. Marcel Dekker Inc., New York, 1982). Area under the plasma concentration versus time curve (AUC) was calculated from the trapezium rule. The AUC from the last data point to time infinity was estimated by extrapolation of the best fit of the full course data. The extrapolated area was a small percentage (<1%) of the total AUC. The results are shown in Table 3.

TABLE 3

Pharmacokinetics of BBNT5 t-PA and CHO wild-type t-PA in the Rabbit Model of Femoral Arterial Thrombosis
Study Date - May 1988

(1) BBNT5 analogue t-PA
Dose 10 mcg/kg/min × 90 min or
3650 IU/kg/min × 90 min i.v

| Rabbit No. | $Cl_s$ (ml/min/kg) | $VD_{ss}$ (ml/kg) | t-½ (min) | $C_{ss}$ (IU/ml) | $C_{ss}$ (ng/ml) |
|---|---|---|---|---|---|
| 1 | 6.17 | 94.7 | 11.80 | 594.4 | 1628.5 |
| 2 | 4.39 | 65.9 | 9.19 | 867.9 | 2377.8 |
| 3 | 3.25 | 57.2 | 10.80 | 1133.2 | 3104.7 |
| 4 | 3.85 | 71.2 | 13.36 | 960.8 | 2632.3 |
| Mean | 4.42 | 72.21 | 11.29 | 889.1 | 2435.8 |
| S.D. | 1.26 | 16.0 | 1.75 | 225.1 | 616.7 |

(2) CHO t-PA 5.32 × $10^5$ IU/mg)
Dose: 10 mcg/kg/min or 5032 IU/kg/min × 90 min. i.v.

| Rabbit No. | $Cl_s$ (ml/min/kg) | $VD_{ss}$ (ml/kg) | t-½ (min) | $C_{ss}$ (IU/ml) | $C_{ss}$ (ng/ml) |
|---|---|---|---|---|---|
| 1 | 25.78 | 218.14 | 1.74 | 214.8 | 426.9 |
| 2 | 24.99 | 104.23 | 2.57 | 222.5 | 422.2 |
| 3 | 24.34 | 161.04 | 2.31 | 231.0 | 459.1 |
| 4 | 24.59 | 71.54 | 2.02 | 215.6 | 427.3 |
| 5 | 24.56 | 157.08 | 3.96 | 219.0 | 432.2 |
| Mean | 24.85 | 142.41 | 2.52 | 220.58 | 433.5 |
| S.D. | 0.57 | 56.52 | 0.86 | 6.58 | 14.7 |

$Cl_s$ = Plasma clearance
$VD_{ss}$ = Volume of distribution at steady-state
$C_{ss}$ = Steady-state concentration based on S-2251 activity assay
t-½ = Post-infusion half-life The plasma levels of BBNT5 thus revealed a half life substantially longer than that typically observed for wild-type t-PA in this model.

Similar infusion studies have been performed for BBNT6 and BBNT12. BBNT6 had a plasma clearance rate of 5.76 ±1.5 ml/min/kg and a t1/2 of 9.9±4.2 minutes while BBNT12 had a plasma clearance rate of 2.8 ±0.1 ml/min/kg and a t1/2 of 13.4±0.7 minutes. Thus, for these analogues also, plasma clearance rates substantially lower than for t-PA and plasma half-lives substantially higher than for t-PA have been observed.

BBNT5, 6, 11 and 12 therefore appear to be unimpaired in enzymic activity and in the ability to lyse clots. The GF domain substitution mutations have resulted in a loss of liver receptor binding that is reflected in a considerably prolonged half-life in plasma. Studies in rabbits have shown these analogues to be superior to t-PA in their ability to lyse blood clots. In contrast, despite having unimpaired enzymic activity in the S2251 assay and not competing for binding to the hepatocyte t-PA receptor, the deletion mutant GF6 was inferior to t-PA in the ability to lyse blood clots.

We claim:

1. A human tissue plasminogen activator analogue comprising the amino acid sequence of native human tissue plasminogen activator, wherein the leucine at amino acid position 66 is substituted with aspartate, the tyrosine at amino acid position 67 is substituted with aspartate, and the phenylalanine at amino acid position 68 is substituted with threonine.

* * * * *